US008915916B2

(12) United States Patent
Duncan

(10) Patent No.: US 8,915,916 B2
(45) Date of Patent: Dec. 23, 2014

(54) INTRAMEDULLARY FIXATION DEVICE FOR SMALL BONE FRACTURES

(75) Inventor: Scott F. M. Duncan, Owatonna, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 774 days.

(21) Appl. No.: 12/434,923

(22) Filed: May 4, 2009

(65) Prior Publication Data

US 2009/0275946 A1 Nov. 5, 2009

Related U.S. Application Data

(60) Provisional application No. 61/050,386, filed on May 5, 2008.

(51) Int. Cl.
| | | |
|---|---|---|
| A61B 17/68 | (2006.01) | |
| A61B 17/72 | (2006.01) | |
| A61B 17/17 | (2006.01) | |
| A61B 17/92 | (2006.01) | |
| A61B 17/00 | (2006.01) | |

(52) U.S. Cl.
CPC ............. *A61B 17/72* (2013.01); *A61B 17/1725* (2013.01); *A61B 17/921* (2013.01); *A61B 2017/00867* (2013.01); *A61B 2017/1775* (2013.01); *A61B 2017/1782* (2013.01)
USPC ............................................... 606/62; 606/78

(58) Field of Classification Search
CPC ....................... A61B 17/72; A61B 2017/00867
USPC .......... 606/62–68, 78, 331, 911, 76, 103, 261, 606/263; 623/21.11
See application file for complete search history.

(56) References Cited

U.S. PATENT DOCUMENTS

| | | |
|---|---|---|
| 3,786,806 A | 1/1974 | Johnson et al. |
| 4,037,324 A | 7/1977 | Andreasen |
| 4,170,990 A | 10/1979 | Baumgart et al. |
| 4,485,816 A | 12/1984 | Krumme |
| 4,550,870 A | 11/1985 | Krumme et al. |
| 4,625,717 A | 12/1986 | Covitz |
| 5,190,546 A | 3/1993 | Jervis |
| 5,246,443 A | 9/1993 | Mai |
| 5,290,289 A | 3/1994 | Sanders et al. |
| 5,474,557 A | 12/1995 | Mai |

(Continued)

*Primary Examiner* — Jan Christopher Merene
*Assistant Examiner* — Atiya Mahmud
(74) *Attorney, Agent, or Firm* — Quarles & Brady, LLP

(57) ABSTRACT

A fracture fixation system particularly useful for bones of the hand and foot is disclosed. The system uses curved shape-memory alloy (e.g., Nitinol) wires that have a predetermined radius of curvature to accommodate different sized bones. These shape-memory alloy wire forms can be inserted into phalanx, metacarpal or metatarsal bones via a percutaneous technique. The technique uses small skin incisions; a specialized drill guide that has holding K-wires to maintain fixation of the drill guide to the bone so that it does not lose the insertion point; a specialized drill as well as a specialized wire cutter and advancement tool to make sure that the level of the wire is below the level of the outer cortical bone. Shape-memory alloy (e.g., Nitinol) based wires with a pre-bent curve have an advantage over the typical standard K-wire in that they can spring back to their predetermined memory shape when inserted into the intramedullary canal of the bone and heated, i.e., a more aggressive curve. By increasing their bending or flexion to increase the arc of curvature, this allows fixation points for the wire, essentially locking it to bone.

16 Claims, 11 Drawing Sheets

(56) References Cited

U.S. PATENT DOCUMENTS

| | | | |
|---|---|---|---|
| 5,722,978 A | 3/1998 | Jenkins, Jr. | |
| 5,743,916 A | 4/1998 | Greenberg et al. | |
| 5,769,856 A | 6/1998 | Dong et al. | |
| 5,779,707 A | 7/1998 | Bertholet et al. | |
| 5,958,159 A | 9/1999 | Prandi | |
| 6,059,789 A | 5/2000 | Dinger et al. | |
| 6,127,597 A | 10/2000 | Beyar et al. | |
| 6,200,321 B1 | 3/2001 | Orbay et al. | |
| 6,268,589 B1 | 7/2001 | Flot | |
| 6,273,892 B1 | 8/2001 | Orbay et al. | |
| 6,279,382 B1 * | 8/2001 | Yatagai | 73/37 |
| 6,323,461 B2 * | 11/2001 | Flot | 219/229 |
| 6,325,805 B1 | 12/2001 | Ogilvie et al. | |
| 6,530,933 B1 | 3/2003 | Yeung et al. | |
| 6,533,788 B1 * | 3/2003 | Orbay | 606/62 |
| 6,616,669 B2 | 9/2003 | Ogilvie et al. | |
| 6,660,009 B1 | 12/2003 | Azar | |
| 6,685,708 B2 | 2/2004 | Monassevitch et al. | |
| 6,908,467 B2 | 6/2005 | Ip et al. | |
| 7,240,677 B2 | 7/2007 | Fox | |
| 7,290,672 B2 * | 11/2007 | Davis et al. | 212/179 |
| 7,811,284 B2 * | 10/2010 | Rabiner et al. | 606/62 |
| 8,475,456 B2 * | 7/2013 | Augoyard et al. | 606/62 |
| 2003/0216739 A1 * | 11/2003 | Ip et al. | 606/72 |
| 2004/0230193 A1 * | 11/2004 | Cheung et al. | 606/63 |
| 2005/0283159 A1 * | 12/2005 | Amara | 606/75 |
| 2006/0064098 A1 * | 3/2006 | Hansson | 606/72 |
| 2006/0129153 A1 * | 6/2006 | Klaue et al. | 606/72 |
| 2007/0066977 A1 | 3/2007 | Assell et al. | |
| 2007/0088412 A1 | 4/2007 | Ashman et al. | |
| 2008/0287950 A1 * | 11/2008 | Frigg et al. | 606/62 |
| 2010/0241120 A1 * | 9/2010 | Bledsoe et al. | 606/62 |

* cited by examiner

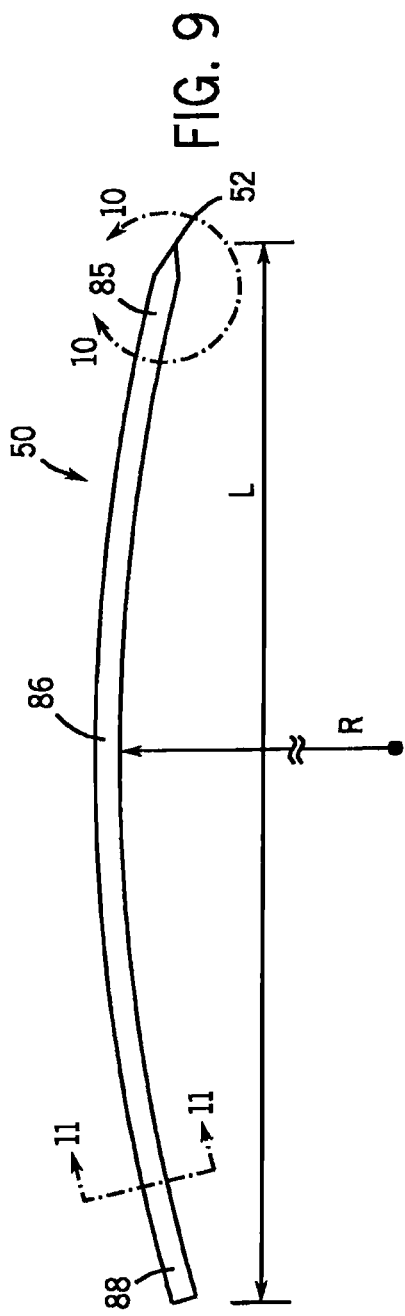
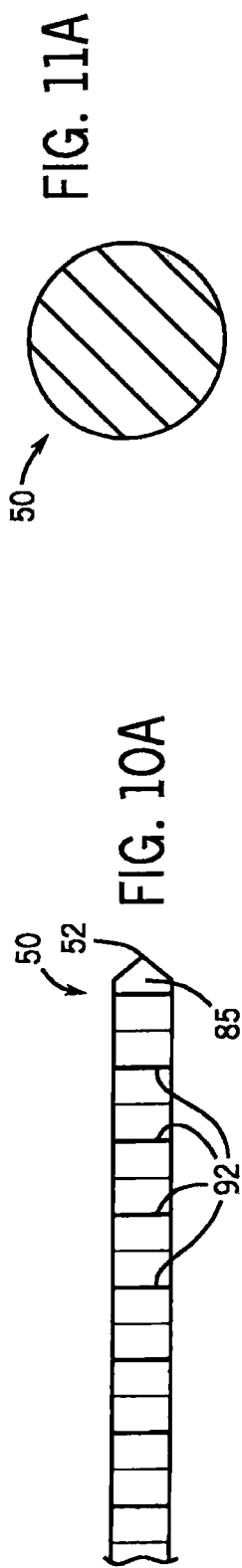
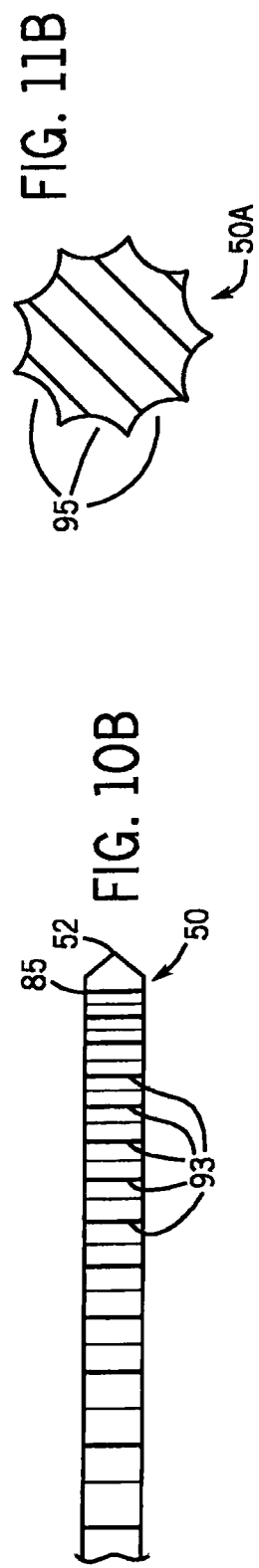
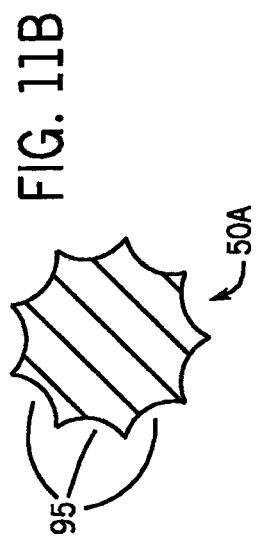
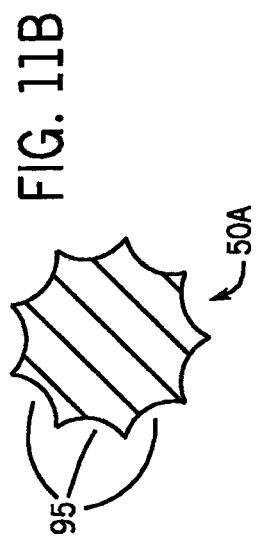

INTRAMEDULLARY FIXATION DEVICE FOR SMALL BONE FRACTURES

CROSS-REFERENCES TO RELATED APPLICATIONS

This application claims priority from U.S. Provisional Patent Application No. 61/050,386 filed May 5, 2008.

STATEMENT REGARDING FEDERALLY SPONSORED RESEARCH

Not Applicable.

BACKGROUND OF THE INVENTION

1. Field of the Invention

The invention relates to methods and devices for the fixation of small bone fractures, and more particularly to methods and devices for the fixation of fractures of the phalangeal, metacarpal, and metatarsal bones.

2. Description of the Related Art

Bones which have been fractured should be immobilized on either side of the fracture for proper healing. Fractures of the phalanges and metacarpals of the hand, and the phalanges and metatarsals of the foot are quite common. Various techniques and fixation devices have been used to maintain proper fracture reduction in the phalangeal, metacarpal, and metatarsal bones.

One fixation method for phalangeal, metacarpal, and metatarsal bones uses plates and screws attached to the bone. A problem with this fixation method for displaced phalanx fractures, metacarpal fractures, and metatarsal fractures is that it requires open reduction with plate and screws which can be quite damaging to the soft tissues and extensor mechanism, limiting the postoperative outcome secondary to the soft tissue scarring.

Another fracture fixation method for phalangeal, metacarpal, and metatarsal bones relies upon the use of Kirschner wires (K-wires) to stabilize the bone at the line of fracture. K-wires are usually left proud above the bone and do not have a fixation point per se. K-wires are left proud so that they can be removed at a later date. These K-wires that are left proud can become infected as well as irritate soft tissue. Because of their lack of point fixation, they can also end up migrating or loosening. This results then in potential loss of the fixation with either malunion or nonunion.

Other methods and devices for the fixation of a fractured metacarpal, metatarsal, or phalangeal bone are described in U.S. Pat. Nos. 6,200,321, 6,273,892 and 6,533,788. This fracture fixation system uses an instrument that includes a main handle and a pin handle movable relative to the main handle. The main handle includes a distal end with a drill, and a longitudinal slot which receives the pin handle. In use, the main handle of the instrument is manipulated to subcutaneously introduce the drill into the metacarpal, metatarsal, or phalangeal bone, and the pin handle is then moved relative to the main handle to introduce a pin into the bone until it extends through the medullary canal on either side of the fracture.

However, there still exists a need for improved methods and devices for the fixation of fractures of the phalangeal, metacarpal, and metatarsal bones wherein the methods and devices can maintain proper fracture reduction with minimal trauma to surrounding tissue.

SUMMARY OF THE INVENTION

The present invention addresses the foregoing needs by providing a system for the fixation of fractures of small bones such as phalangeal, metacarpal, and metatarsal bones. The system uses curved shape-memory alloy (e.g., Nitinol) wires that have a predetermined radius of curvature to accommodate different sized bones. Multiple sizes of the wires can be included in a kit. These shape-memory alloy wire forms are inserted into phalanx, metacarpal or metatarsal bones via a percutaneous technique. The technique uses small skin incisions; a specialized drill guide that has holding K-wires to maintain fixation of the drill guide to the bone so that it does not lose the insertion point; a specialized drill as well as a specialized wire cutter and advancement tool to make sure that the level of the wire is below the level of the outer cortical bone. Shape-memory alloy (e.g., Nitinol) based wires with a pre-bent curve have an advantage over the typical standard K-wire in that they can be allowed to spring back to their predetermined shape when inserted into the intramedullary canal of the bone and heated, i.e., a more aggressive curve. By increasing their bending or flexion to increase the arc of curvature, this allows fixation points for the wire form, essentially locking it to bone. This solves a problem with typical straight K-wire fixation that does not have locking points that prevent movement or migration of the wire-bone construct.

Shape-memory alloy (e.g., Nitinol) wires in suitable diameters are commercially available; however, they do not have the memory curve "programmed" into them and they are not surgical grade. The main consideration with altering the diameters of the wire is in the amount of radius curvature that is built into the metallic memory. One advantage of the shape-memory alloy (e.g., Nitinol) intramedullary device is that the change of shape, i.e., increasing curvature of the wire upon implantation finds fixation points as it pressed against the bone. Straight K-wires again, have the disadvantage of acting only in an axial fashion. One of the advantages of the curved system is the instrumentation. This instrumentation uses a unique drill guide that can be essentially locked into position on the bone with supplemental traditional Kirchner wires.

Also, the use of a specialized drill prevents over penetrating of the bone. This drill also has a specialized tip that allows it to catch on the bone preventing the usual movement of the drill once it starts because of the torque from the drill bit forcing the drill to move off of the bone. A shoulder ledge on the drill is used to prevent over penetration. Once the bone has essentially been close reduced and the drill guide placed through a small incision in the drill used to penetrate the cortex, the intramedullary device is advanced in through a hand toggling system. This can be checked under fluoro-imaging to make sure that it was advancing appropriately across the fracture site. It is advanced only up to a certain point so that the wire can be then further advanced once it had been cut to fit completely in the bone. Once the wire is imaged and perceived to be in the appropriate position, the shape-memory alloy is heated to restore its memory and increase its curvature points. The guide is then reduced and a special wire cutter cuts the intramedullary nail very close to the bone. The guide can then be reapplied along the same previous K-wires that were there and then a wire advancement tool used through the drill guide to push the remaining wire into the bone so that it sits at or below the level of the cortical surface. The wire advancement tool can have a special groove in the base of it to catch the bump or ridge left by the wire cutter to help facilitate maintaining some rotational control. An alternative means is to precut or cut prior to heating the metal. This then advances the intramedullary device into the bone again prior to the memory being activated. The memory can then be activated by drilling two specialized wire probes to touch two different sections of the intramedullary device and then applying the heating electrical charge through these two percutaneous wires that were then touching the shape-memory alloy in the bone.

Current methods for treating metacarpal and metatarsal fractures intramedullary with K-wires involve making an incision over the proximal aspect of the bone and drilling a hole in it large enough so that the wire can be advanced down the intramedullary canal. With shape-memory alloy intramedullary devices it is possible to insert this through the dorsal superior aspect of the metacarpal and metatarsal heads. This precludes the need for drilling a large hole into the bone. Instead this wire can be advanced and once it was passed the fracture site and engages the dorsal cortex, the memory can be activated, the wire cut at the level of the chondral bone and then again with the advancement tool, advanced another millimeter or two. It can be quite easy to insert, certainly one if not two of these wires down the intramedullary canal in this fashion providing a fixation not only for diaphyseal type metacarpal and metatarsal fractures, but for also the more challenging metacarpal neck fractures, i.e., boxer fracture. Boxer fractures in this country are quite common. However, they can be challenging to treat in that there usually is not adequate bone distally for a traditional plate and screw fixation and that K-wire fixation with proud wires sticking through the skin can potentially lead to deep infections of the joint or soft tissues, or a significant irritation with scarring and/or stiffness of the small finger itself. This invention can preclude these types of problems by providing intramedullary fixation, which allows for early active range of motion, improving patient outcomes.

Thus, in one aspect, the invention provides a fracture fixation system for a bone such as a phalangeal, metacarpal or metatarsal bone. The system includes a wire form comprising a shape memory alloy that has an austenitic phase structure above a first temperature and a martensitic phase structure below a second temperature. The shape memory alloy can be a nickel-titanium shape-memory alloy. The wire form is provided in the martensitic phase structure in a shape including an arcuate portion having a first radius of curvature. The wire form has a first end and an opposite second end. The arcuate portion can extend from the first end to the second end of the wire form. The wire form is dimensioned such that the wire form can be located in an intramedullary canal of the bone with the first end adjacent a distal end of the intramedullary canal of the bone and the second end adjacent a proximal end of the intramedullary canal of the bone. The arcuate portion of the wire form can have a second radius of curvature when the wire form is in the austenitic phase. The second radius of curvature is smaller than the first radius of curvature. In one version of the wire form, the second radius of curvature is small enough such that an intermediate section of the wire form contacts one side of an inner surface of the intramedullary canal, and the first end and the second end of the wire form contact an opposite side of the inner surface of the intramedullary canal. Also, a tip of the wire form can have spaced apart tip portions when the wire form is in the austenitic phase. Thus, the wire form opens at the tip to lock itself into bone.

The wire form can have a transverse cross-section in the form of a circle, oval, ellipsis, rectangle, square, pentagon, or hexagon. In one version of the wire form, the wire form has a transverse cross-section in the form of a circle. The first end of the wire form can terminate in a point. In one version of the wire form, the surface of the wire form includes threads. In another version of the wire form, the surface of the wire form includes slots.

In another aspect, the invention provides a fracture fixation system for a bone such as a phalangeal, metacarpal or metatarsal bone. The system includes a wire form comprising a shape memory alloy that has an austenitic phase structure above a first temperature and a martensitic phase structure below a second temperature. The shape memory alloy can be a nickel-titanium shape-memory alloy. The wire form is provided in the austenitic phase structure in a shape including an arcuate portion having a first radius of curvature. The wire form has a first end and an opposite second end. The arcuate portion can extend from the first end to the second end of the wire form. The wire form is dimensioned such that the wire form can be located in an intramedullary canal of the bone with the first end adjacent a distal end of the intramedullary canal of the bone and the second end adjacent a proximal end of the intramedullary canal of the bone.

The wire form can have a transverse cross-section in the form of a circle, oval, ellipsis, rectangle, square, pentagon, or hexagon. In one version of the wire form, the wire form has a transverse cross-section in the form of a circle. The first end of the wire form can terminate in a point. In one version of the wire form, the surface of the wire form includes threads. In another version of the wire form, the surface of the wire form includes slots.

In still another aspect, the invention provides a method for fixing a bone having a fracture such as a phalangeal, metacarpal or metatarsal bone. The method uses a wire form comprising a shape memory alloy that has an austenitic phase structure above a first temperature and a martensitic phase structure below a second temperature. The shape memory alloy can be a nickel-titanium shape-memory alloy. The wire form is provided in the martensitic phase structure in a shape including an arcuate portion having a first radius of curvature. The wire form is inserted into an intramedullary canal of the bone such that a first end of the wire form is positioned on a distal side of the fracture and a second end of the wire form is positioned on a proximal side of the fracture. During insertion or after insertion of the wire form into the intramedullary canal of the bone, the wire form is heated above the first temperature to convert the wire form to the austenitic phase structure and transform the arcuate portion of the wire form to a second radius of curvature less than the first radius of curvature.

The wire form can be heated by applying electric current to the wire form after insertion of the wire form into the intramedullary canal of the bone. In the method, a guide bore can be created in the bone to create a pathway from an outer surface of the bone to the intramedullary canal of the bone. The guide bore can be created by placing a drill guide having a drill bit guide hole over an end of the bone and advancing a drill bit through the drill bit guide hole and into the bone. The drill guide can include a wire hole and the drill guide is secured to the end of the bone by advancing a wire through the wire hole and into the bone. The wire form can be cut adjacent an outer surface of the bone after insertion of the wire form into the intramedullary canal of the bone, and a cut end of the wire form can be pushed to or below the outer surface of the bone after cutting the wire form.

In yet another aspect, the invention provides a method for fixing a bone having a fracture such as a phalangeal, metacarpal or metatarsal bone. The method uses a wire form comprising a shape memory alloy that has an austenitic phase structure above a first temperature and a martensitic phase structure below a second temperature. The shape memory alloy can be a nickel-titanium shape-memory alloy. The wire form is provided in the austenitic phase structure in a shape including an arcuate portion. The wire form is cooled below the second temperature such that the wire form is in the martensitic phase structure. The arcuate portion of the wire form is then deformed to a first radius of curvature before or during inserting the wire form into an intramedullary canal of the bone such that a first end of the wire form is positioned on a distal side of the fracture and a second end of the wire form is positioned on a proximal side of the fracture. During insertion or after insertion of the wire form into the intramedullary canal of the bone, the wire form is heated above the first temperature to convert the wire form to the austenitic phase structure and transform the arcuate portion of the wire form to a second radius of curvature less than the first radius of curvature. The wire form can be heated by body heat after insertion of the wire form into the intramedullary canal of the bone.

In the method, a guide bore can be created in the bone to create a pathway from an outer surface of the bone to the intramedullary canal of the bone. The guide bore can be created by placing a drill guide having a drill bit guide hole over an end of the bone and advancing a drill bit through the drill bit guide hole and into the bone. The drill guide can include a wire hole and the drill guide is secured to the end of the bone by advancing a wire through the wire hole and into the bone. The wire form can be cut adjacent an outer surface of the bone after insertion of the wire form into the intramedullary canal of the bone, and a cut end of the wire form can be pushed to or below the outer surface of the bone after cutting the wire form.

In still another aspect, the invention provides a kit including components for fixing a bone having a fracture such as a phalangeal, metacarpal or metatarsal bone. The kit can include at least one of the following: (i) a wire form for insertion into the intramedullary canal of the bone; (ii) a drill guide having a drill bit guide hole and at least one wire hole for accepting a wire that is advanced through the wire hole and into the bone; (iii) a drill bit having a specialized pointed tip that allows it to catch on the bone preventing the usual movement of the drill once it starts; (iv) a drill having a shoulder ledge on the drill that is used to prevent over penetration of the drill bit into the bone; and (v) means for applying electric current to the wire such as an electrical power supply connected to a pair of probes that can be placed in contact with the opposite ends of the wire form.

Thus, the invention provides methods and devices for the fixation of small bone fractures such as fractures of the phalangeal, metacarpal, and metatarsal bones.

These and other features, aspects, and advantages of the present invention will become better understood upon consideration of the following detailed description, drawings, and appended claims.

BRIEF DESCRIPTION OF THE DRAWINGS

FIG. 9 is a side view of one embodiment of a wire form according to the invention.

FIG. 10A is a detailed view of a wire form according to the invention taken along line 10-10 of FIG. 9.

FIG. 10B is a detailed view of another embodiment of a wire form according to the invention taken along line 10-10 of FIG. 9.

FIG. 11A is a cross-sectional view of a wire form according to the invention taken along line 11-11 of FIG. 9.

FIG. 11B is a cross-sectional view of another embodiment of a wire form according to the invention taken along line 11-11 of FIG. 9.

Like reference numerals will be used to refer to like parts from Figure to Figure in the following description of the drawings.

DETAILED DESCRIPTION OF THE INVENTION

Figure 1:
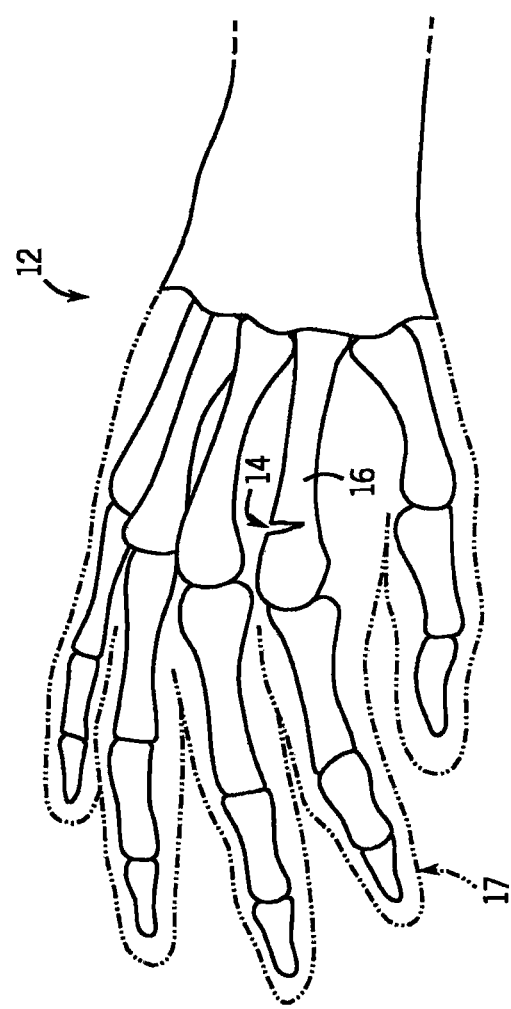
FIG. 1 is a perspective view of a right human hand having a fracture in the second metacarpal.

Looking first at FIG. 1, there is shown a right human hand 12 having a fracture 14 in the second metacarpal 16 in the index finger 17. The method and devices according to the invention can be used for fixation of the fracture 14 of the second metacarpal 16 to maintain proper fracture reduction for healing. While the use of methods and devices according to the invention has been shown and described herein with reference to a fracture 14 of the second metacarpal 16, it should be appreciated that the methods and devices according to the invention can be used for the fixation of other small bone fractures, such as fractures of any of the phalangeal, metacarpal, and metatarsal bones. Also, while the methods and devices according to the invention shown and described herein only use a single wire form, one or more wire forms may be inserted into the intramedullary canal of the bone in the method.

Figure 2:
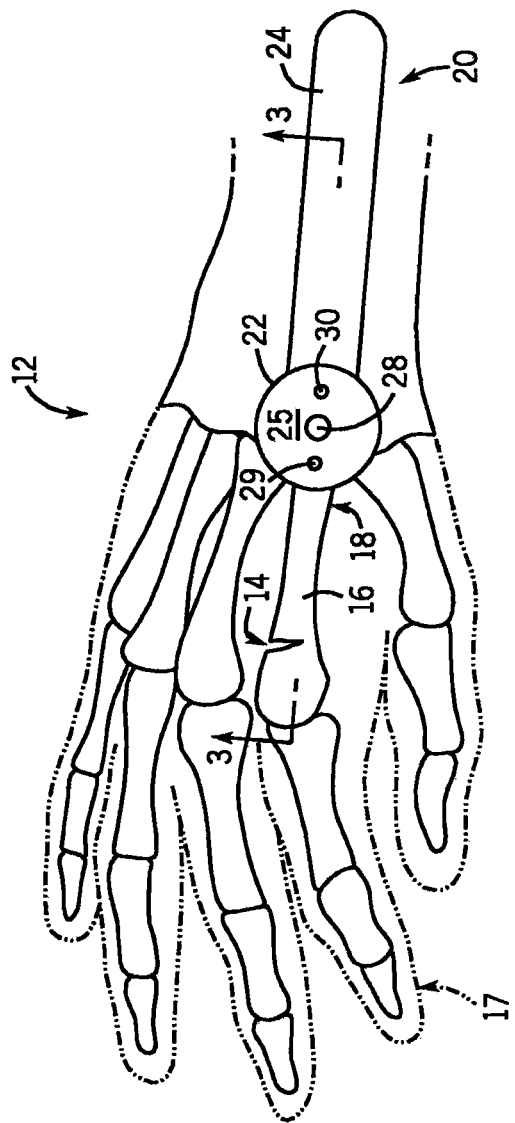
FIG. 2 is a view of the hand of FIG. 1 with a drill guide according to the invention positioned on the hand for use.
Figure 3:
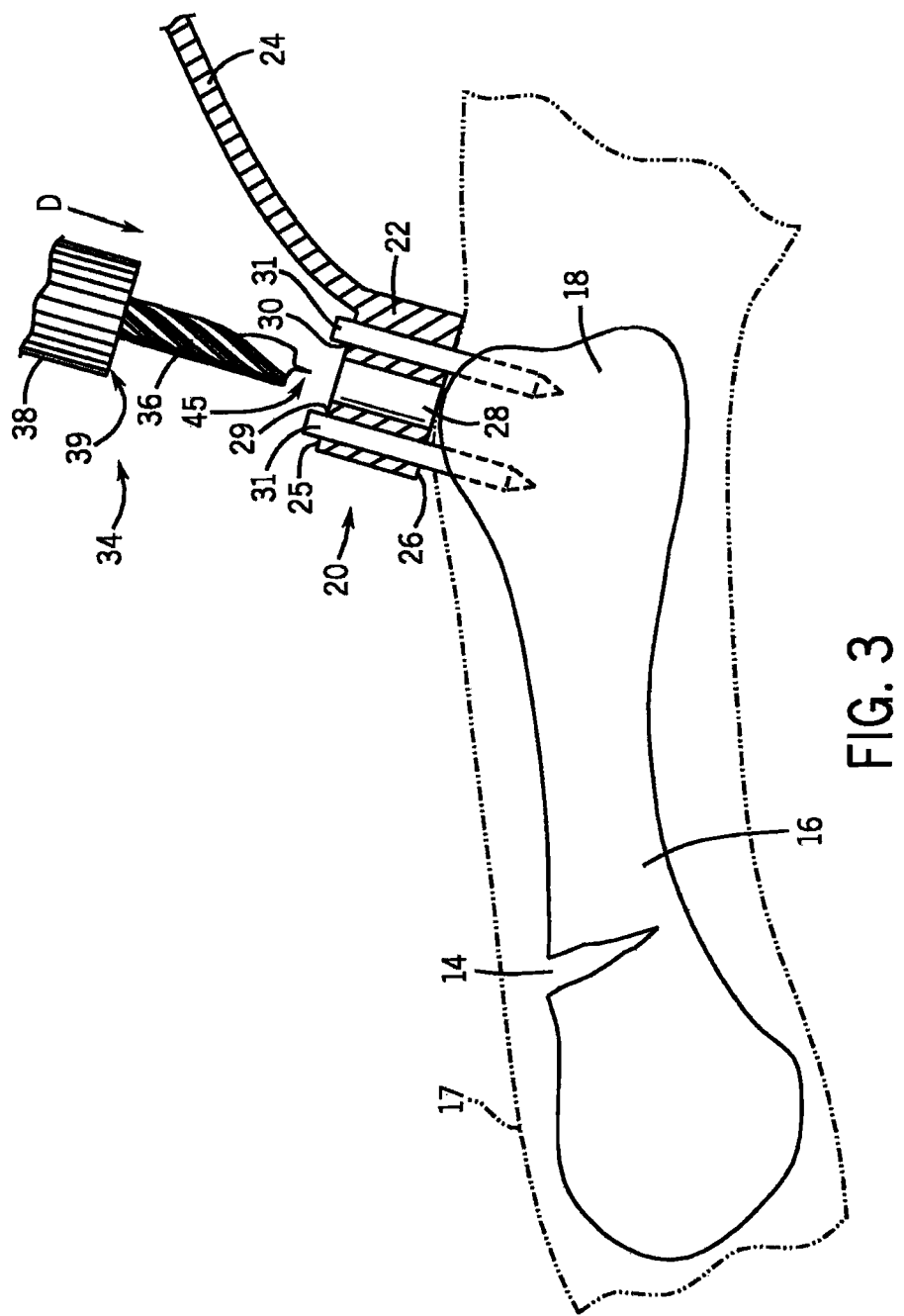
FIG. 3 is a lateral cross-sectional view taken along line 3-3 of FIG. 2.

In the method of the invention, an incision is first made in the skin and tissue overlying the proximal end 18 of the second metacarpal 16. A drill guide 20 according to the invention is then placed over the incision as shown in FIGS. 2 and 3. The drill guide 20 has a generally cylindrical base 22 and a handle 24 that is connected to the base 22. The handle 24 allows for placement of the base 22 over the incision. The base 22 of the drill guide 20 has a top surface 25 and a bottom surface 26. A central drill bit guide hole 28 extends through the base 22 from the top surface 25 to the bottom surface 26. A pair of wire holes 29, 30 also extend through the base 22 from the top surface 25 to the bottom surface 26 on opposite sides of the drill bit guide hole 28. The drill guide 20 may be formed from suitable material such as stainless steel. The surgeon can locate the drill guide 20 over the incision such that the drill bit guide hole 28 is aligned with the incision. K-wires 31 are inserted through the wire holes 29, 30 of the base 22 of the drill guide 20 and into the proximal end 18 of the second metacarpal 16 to secure the drill guide 20 to the proximal end 18 of the second metacarpal 16. In an example form of the drill guide 20, the drill bit guide hole 28 is sized at 4 millimeters to accommodate a 2 millimeter diameter drill bit, and the wire holes 29, 30 are sized to accommodate 0.035 inch diameter K-wires.

Looking at FIG. 3, a drill 34 having a drill bit 36 mounted in a chuck 38 is used to create a guide bore in the proximal end 18 of the second metacarpal 16. The chuck 38 of the drill 34 has a shoulder 39 that contacts the top surface 25 of the base 22 of the drill guide 20 when the drill bit 36 is advanced in direction D in the central drill bit guide hole 28 of the drill guide 20. The top surface 25 of the base 22 of the drill guide 20 stops movement in direction D of the shoulder 39 thereby limiting the depth of the guide bore 41 (see FIG. 4). However, the guide bore 41 created by the drill bit 36 creates a pathway to the intramedullary canal 43 of the second metacarpal 16. The intramedullary canal 43 has an inner surface 44. Preferably, the drill bit 36 has a wire point 45 to facilitate holding the drill bit 36 on the surface of the proximal end 18 of the second metacarpal 16. After drilling the guide bore 41, the surgeon may remove the drill guide 20 from the proximal end 18 of the second metacarpal 16.

Figure 4:
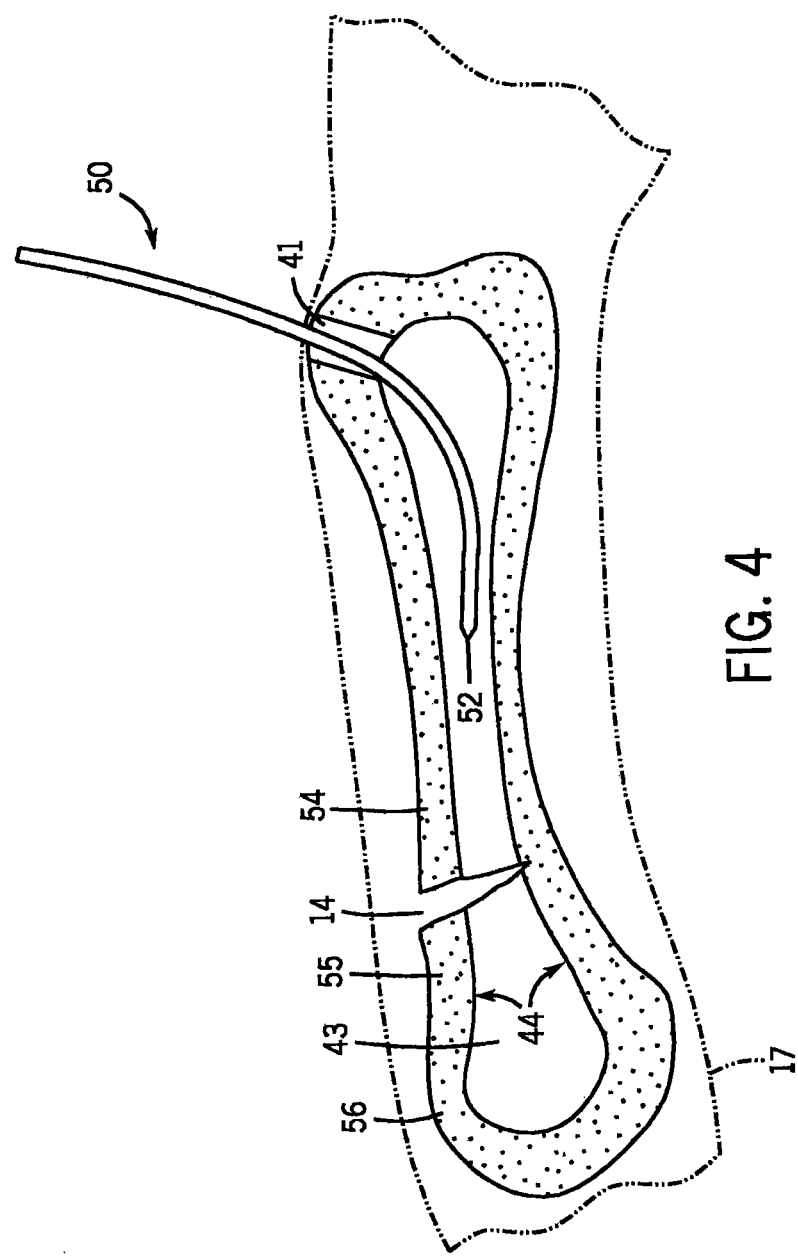
FIG. 4 is a lateral view similar to FIG. 3 showing a wire form according to the invention being inserted into the intramedullary canal of the second metacarpal of the hand of FIG. 1.
Figure 5:
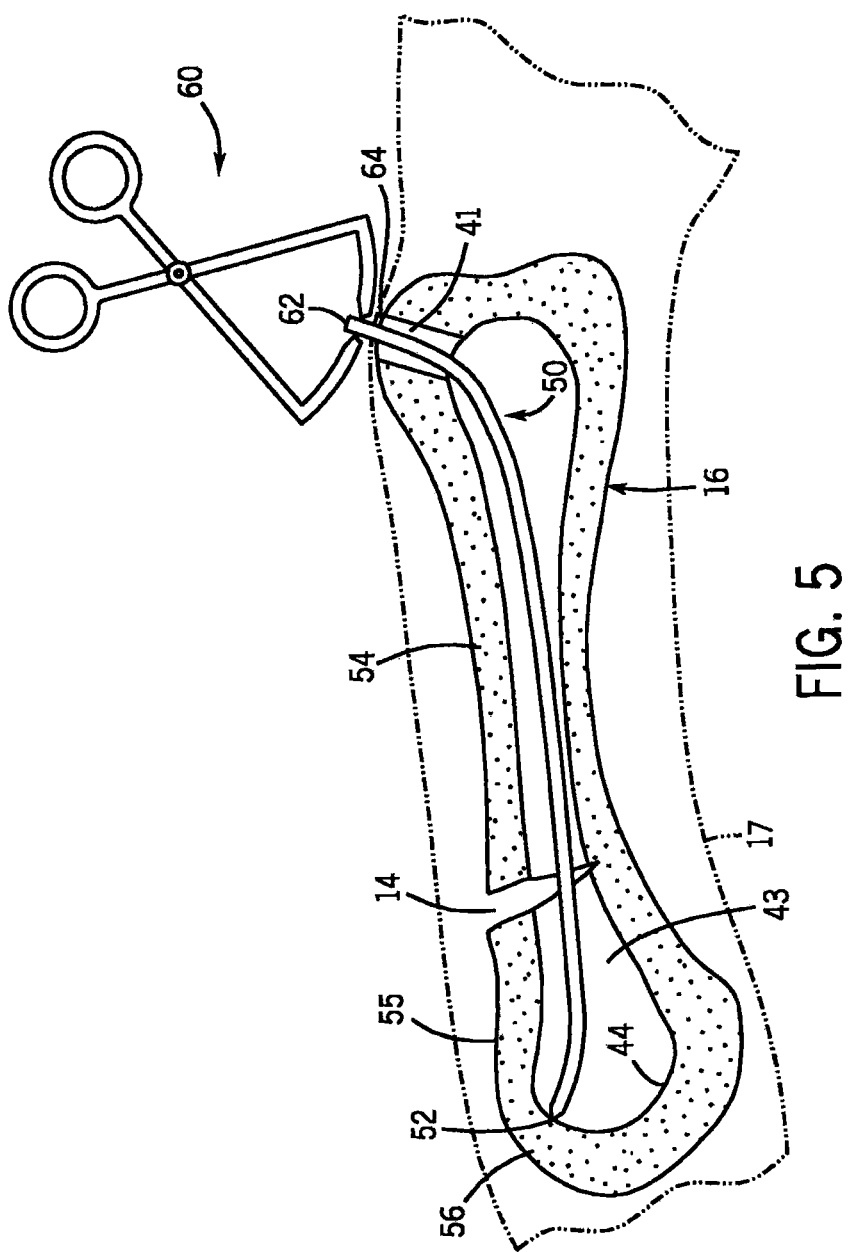
FIG. 5 is a lateral view similar to FIG. 4 showing the end of a wire form according to the invention being cut after insertion of the wire into the intramedullary canal of the second metacarpal of the hand of FIG. 1.
Figure 6:
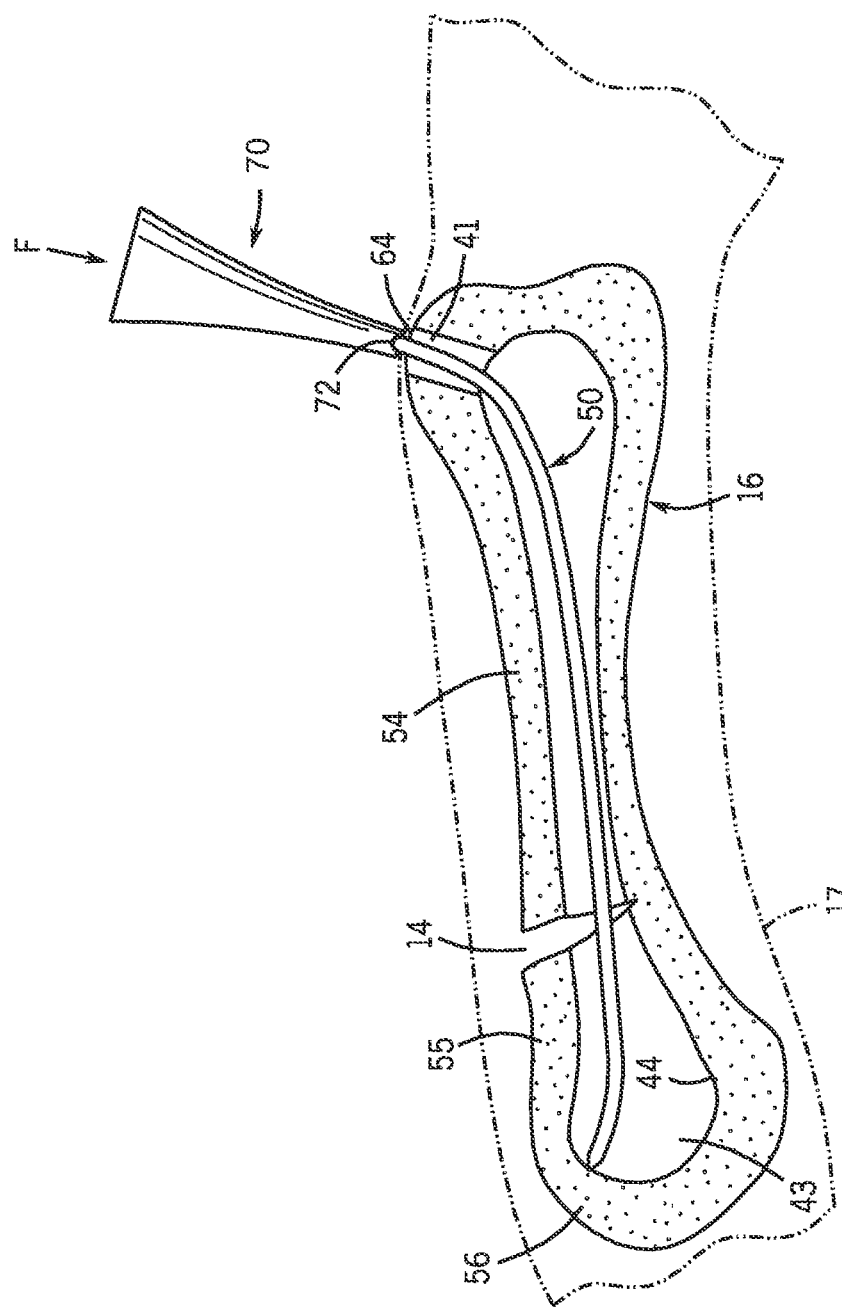
FIG. 6 is a lateral view similar to FIG. 5 showing the end of a wire form according to the invention being advanced further into the intramedullary canal of the second metacarpal of the hand of FIG. 1.

Turning now to FIG. 4, a wire form 50 according to the invention is advanced through the wire guide bore 41 and into the intramedullary canal 43 of the second metacarpal 16 with the use of fluoroscopy. The wire form 50 is advanced through the proximal fragment 54, passed the fracture 14 and into the distal fragment 55 of the second metacarpal 16. The tip 52 of the wire form 50 is then advanced to the head 56 of the second metacarpal 16 as shown in FIG. 5. Referring to FIG. 5, a wire cutter 60 is then used to cut the proximal end 62 of the wire form 50 close to the outer surface 64 of the proximal end 18 of the second metacarpal 16. The wire cutter 60 includes cutting surfaces that create a generally domed cut end of the wire form 50. Turning to FIG. 6, an advancement tool 70 having a concave tip 72 is used to advance the proximal end 62 of the wire form 50 to or below the outer surface 64 of the proximal end 18 of the second metacarpal 16 by way of movement in direction F.

Figure 7:
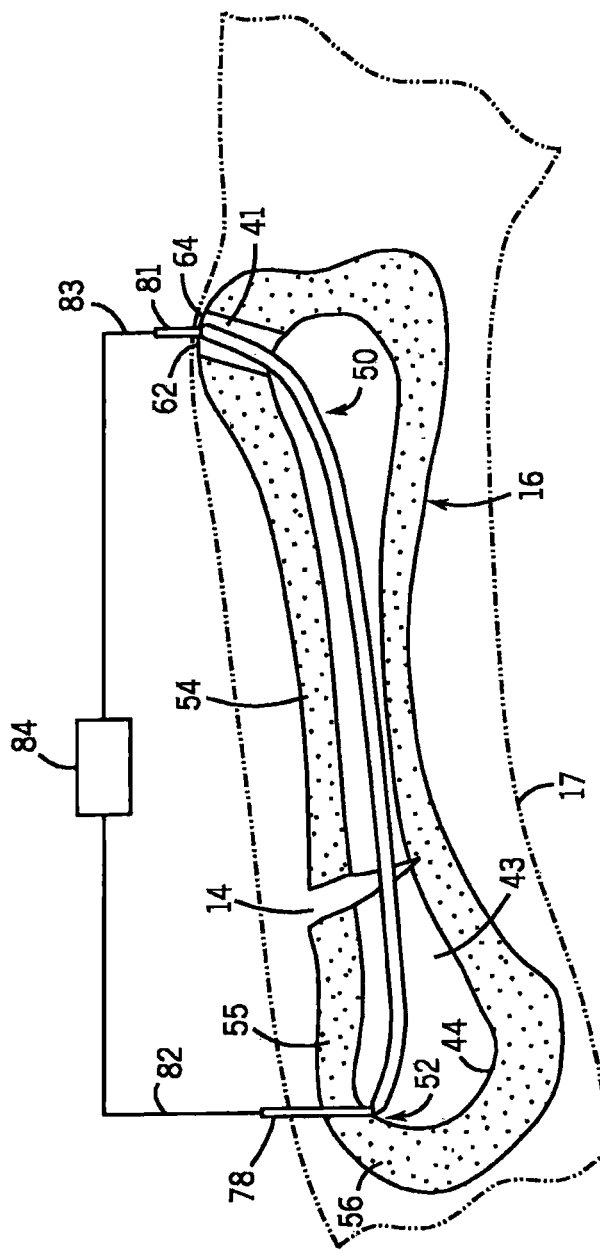
FIG. 7 is a lateral view similar to FIG. 6 showing the ends of a wire form according to the invention being placed in an electrical circuit with a power supply after insertion of the wire into the intramedullary canal of the second metacarpal of the hand of FIG. 1.

Referring now to FIG. 7, the tip 52 of the wire form 50 is placed in electrical contact with a first probe 78 (by way of a suitable hole created in the second metacarpal 16). Also, the proximal end 62 of the wire form 50 is placed in electrical contact with a second probe 81. The first probe 78 and the second probe 81 are in electrical communication via lines 82,83 respectively with an electrical power supply 84. The power supply 84 is turned on to introduce electrical current into the wire form 50 to heat the wire form 50 due to the resistivity of the wire form.

The wire form 50 preferably comprises a nickel-titanium shape-memory alloy which is biocompatible and corrosion resistant. The shape-memory alloy has different phase structures at different temperatures. At a lower temperatures, the alloy is martensitic. At a higher temperatures, the alloy is austenitic. When a martensitic alloy is heated up to a temperature $A_{low}$, the austenitic phase begins to form. Above a higher temperature $A_{high}$, the alloy is fully austenitic. When an austenitic alloy is cooled down to a temperature $M_{high}$, the martensitic phase begins to form. Below a lower temperature $M_{low}$, the alloy is fully martensitic. An example nickel-titanium shape-memory alloy includes 50-57 weight percent nickel and 43-50 weight percent titanium.

An example shape of the wire form 50 is shown in FIG. 9. The wire form 50 has a chord length L and is in the form of an arc having a radius of curvature R. The wire form 50 has a first distal end 85 and an intermediate section 86 and a second proximal end 88. The arc extends from the first distal end 85 to the second proximal end 88 of the wire form 50; however, less then the entire length L may include an arc and multiple different arced sections may be used. The distal end 85 of the wire form 50 may terminate in a point 52 (see FIG. 10A). The surface 87 of the wire form 50 may include threads 92 (see FIG. 10A) or variable pitch threads 93 (see FIG. 10B). The cross-section of the wire form 50 may take various forms. For example, FIG. 11A shows a wire form 50 with a circular transverse cross-section, while FIG. 11B shows a wire form 50A with longitudinal slots 95 in the outer surface of the wire form 50A to aid in gripping the surface of the intramedullary canal 43 of the second metacarpal 16. It should be appreciated that the invention is not limited to the shapes of the wire form 50 and 50A shown. Other non-limiting example cross-section shapes include oval, elliptical, rectangular, square, pentagonal, and hexagonal. The dimensions of the cross-section may also vary along the length of the wire form 50 or 50A. In non-limiting example forms, the diameter of a uniform round cross-section wire form ranges from 0.004 inches to 0.102 inches, preferably the diameter ranges from 0.020 inches to 0.090 inches, more preferably the diameter ranges from 0.030 inches to 0.080 inches, and most preferably the diameter ranges from 0.040 inches to 0.070 inches. In non-limiting example forms, the thickness and width of a uniform square or rectangular cross-section wire form ranges from 0.002 inches to 0.102 inches for thickness and 0.002 inches to 0.102 inches for width.

The temperature-dependent phase structure of the alloy comprising the wire form 50 gives rise to a shape memory property in the wire form 50. At the fully austenitic phase, a wire of the alloy can be formed into a wire form of a given shape and can be treated to memorize that shape and return to that memorized shape whenever in the austenitic phase. The wire form is then cooled to a martensitic phase and plastically deformed in the martensitic phase. When heated back to the austenitic phase, the wire form is will resume its memorized austenitic shape.

Figure 12B:
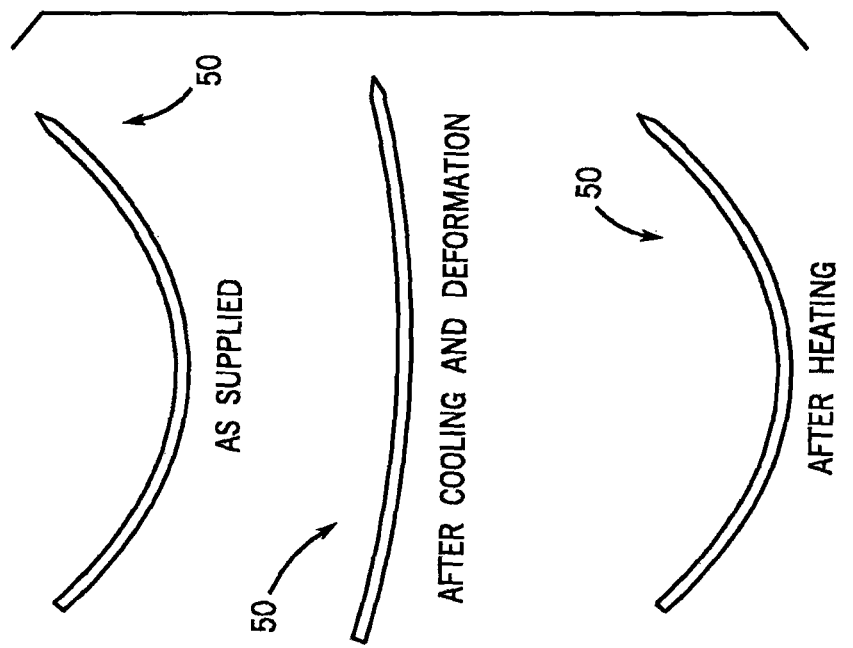
FIG. 12B shows another version of a wire form according to the invention before cooling and deformation, and after heating.
Figure 12A:
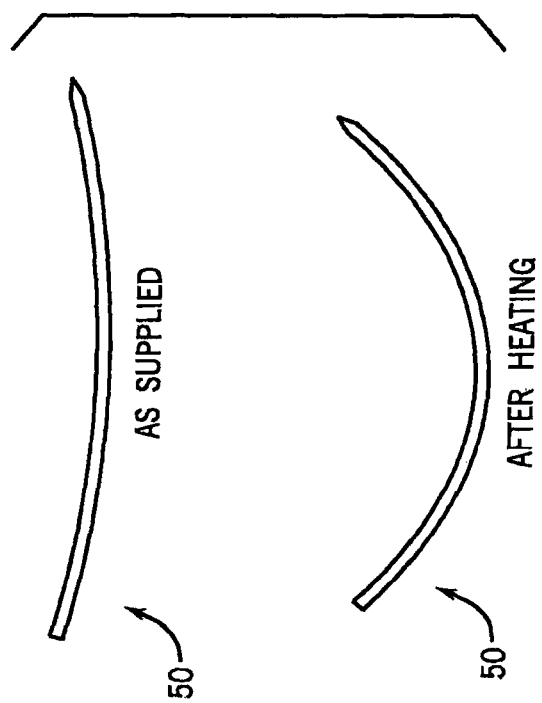
FIG. 12A shows one version of a wire form according to the invention before and after heating.

In one version of the invention, the wire form 50 is provided in a fully martensitic phase at a first temperature (which may be room temperature—72° F.). The wire form 50 is provided in a first martensitic shape including a first martensitic arcuate portion of a first martensitic radius of curvature. The first martensitic arcuate portion may comprise some or all of the wire form 50. The wire form 50 is inserted into the intramedullary canal 43 of the second metacarpal 16 and may undergo some deformation from the first martensitic shape when advanced into the intramedullary canal 43 of the second metacarpal 16. After insertion into the intramedullary canal 43 of the second metacarpal 16, the wire form 50 is heated to a higher second temperature above $A_{high}$ to transform to the wire form 50 to a first austenitic shape. The first austenitic shape includes a first austenitic arcuate portion of a first austenitic radius of curvature that is smaller than the first martensitic radius of curvature of the first martensitic arcuate portion of the first martensitic shape. In other words, the transformation from martensite to austenite moves at least an arcuate portion of the wire form 50 from a martensitic shape of higher radius of curvature toward a lower radius of curvature that is nearer or at the size of a radius of curvature of an arcuate portion of the memorized austenitic shape. The heating to the higher second temperature above $A_{high}$ can occur from the introduction of electrical current from the power supply 84 into the wire form 50 to heat the wire form 50 due to the resistivity of the wire form 50. The wire form 50 then cools down to body temperature which is above $M_{high}$ such that the wire form 50 remains in the austenitic shape. The shape transformation in this version of the invention is depicted in FIG. 12A. In the "as supplied" martensitic shape of FIG. 12A, the radius of curvature for the wire form 50 is greater than the radius of curvature for the "after heating" austenitic shape of the wire form 50.

In another version of the invention, the wire form 50 is provided in a fully austenitic phase at a first temperature (which may be room temperature–72° F.). The wire form 50 is provided in a first austenitic ("memorized") shape including a first austenitic arcuate portion of a first austenitic radius of curvature. The first austenitic arcuate portion may comprise some or all of the wire form 50. The wire form 50 is cooled to a temperature below $M_{low}$ and deformed to a first martensitic shape including a first martensitic arcuate portion of a first martensitic radius of curvature that is greater than the first austenitic radius of curvature of the first austenitic arcuate portion of the first austenitic shape. Stated in another way, the first austenitic arcuate portion of the first austenitic ("memorized") shape is straightened at least a small amount. The deformed wire form 50 is inserted into the intramedullary canal 43 of the second metacarpal 16. After insertion into the intramedullary canal 43 of the second metacarpal 16, the wire form 50 is naturally heated to body temperature (~98.6° F.). Since the body temperature is above $A_{high}$, the wire form 50 transforms to a second austenitic shape that includes a second austenitic arcuate portion of a second austenitic radius of curvature that is smaller than the first martensitic radius of curvature of the first martensitic arcuate portion of the first martensitic shape. In other words, the transformation back to the austenitic phase moves at least an arcuate portion of the wire form 50 from a martensitic shape of higher radius of curvature toward a lower radius of curvature that is nearer or at the size of the first austenitic radius of curvature of the first austenitic arcuate portion of the first austenitic shape. The shape transformation in this version of the invention is depicted in FIG. 12B. In the "as supplied" austenitic shape of FIG. 12B, the radius of curvature for the wire form 50 is less than the radius of curvature for the "after cooling and deformation" martensitic shape of the wire form 50. In the "after cooling and deformation" martensitic shape of the wire form 50 of FIG. 12B, the radius of curvature for the wire form 50 is greater than the radius of curvature for the "after heating" austenitic shape of the wire form 50.

Figure 8:
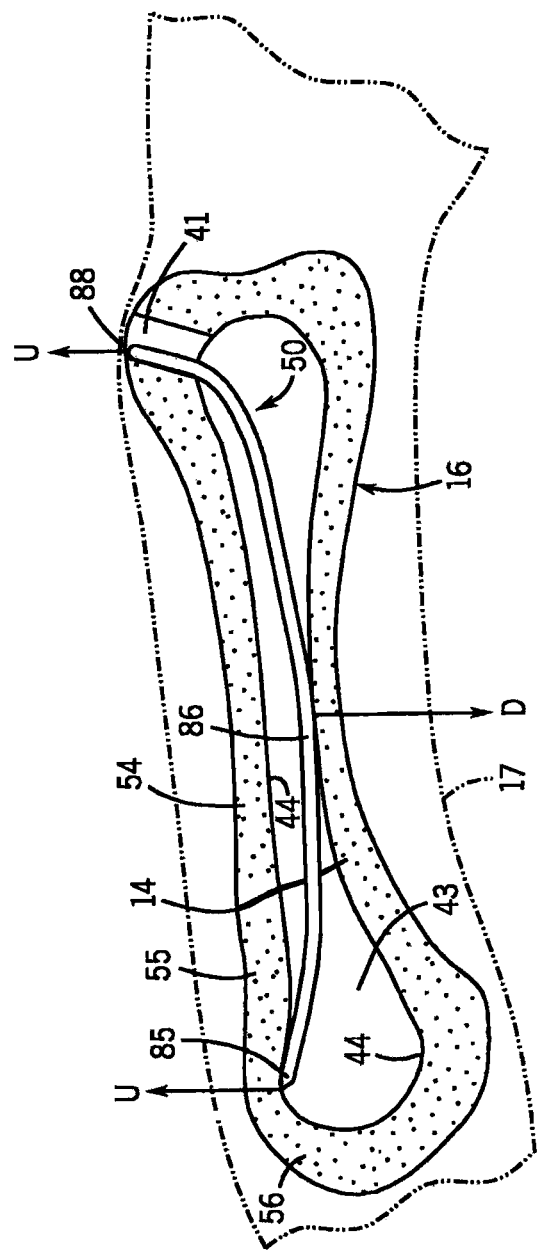
FIG. 8 is a lateral view similar to FIG. 7 showing a wire form according to the invention in a final position in the intramedullary canal of the second metacarpal of the hand of FIG. 1.

Looking now at FIG. 8, the wire form 50 is shown after heating, the intermediate section 86 of the wire form 50 contacts one side of the inner surface 44 of the intramedullary canal 43, and the first end 85 and the second end 88 of the wire form 50 contact an opposite side of the inner surface 44 of the intramedullary canal 43. The shape memory of the wire form 50 (which seeks a smaller radius of curvature) urges the intermediate section 86 of the wire form 50 in direction D and the first end 85 and the second end 88 of the wire form 50 in direction U. This serves to pull the proximal fragment 54 and the distal fragment 55 together. Also, it wedges the wire form 50 in the intramedullary canal 43. Further, any projections on the end surfaces of the first end 85 and the second end 88 of the wire form 50 engage the inner surface 44 of the intramedullary canal 43.

Figure 12C:
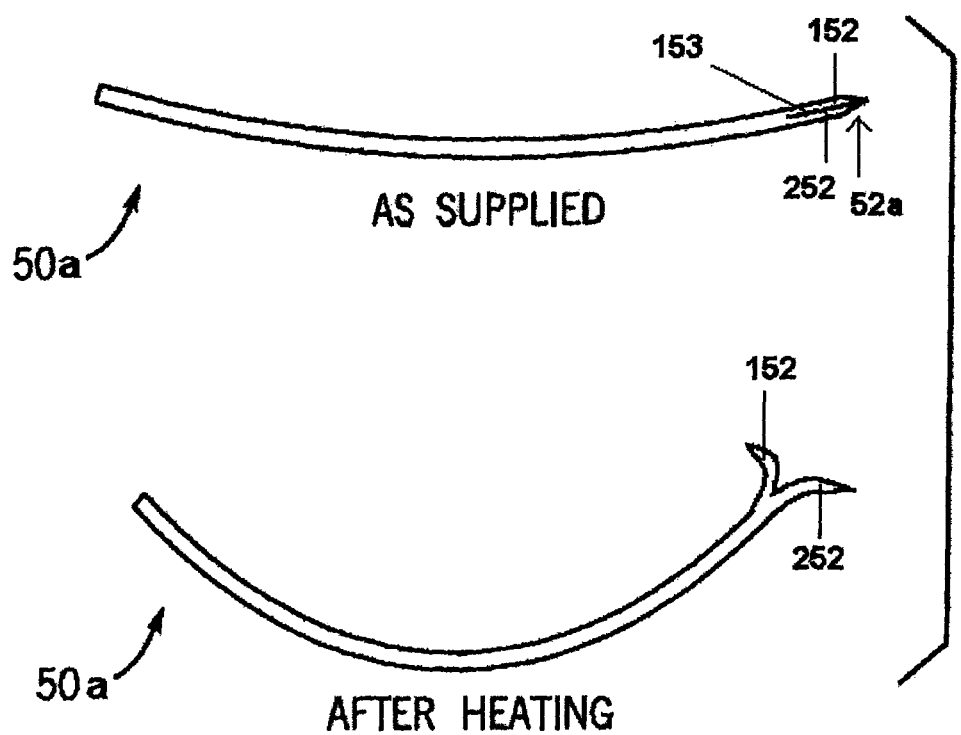
FIG. 12C shows still another version of a wire form according to the invention before and after heating.

Looking at FIG. 12C, a wire form 50a can be supplied in a fully martensitic phase at a first temperature (which may be room temperature–72° F.). The wire form 50a is provided in a first martensitic shape including a first martensitic arcuate portion of a first martensitic radius of curvature. The first martensitic arcuate portion may comprise some or all of the wire form 50a. In the first martensitic shape, the tip 52a of the wire form 50a includes a first tip portion 152 separated from a second tip portion 252 by a separation line 153. The wire form 50a is inserted into the intramedullary canal 43 of the second metacarpal 16 and may undergo some deformation from the first martensitic shape when advanced into the intramedullary canal 43 of the second metacarpal 16. After insertion into the intramedullary canal 43 of the second metacarpal 16, the wire form 50a is heated to a higher second temperature above $A_{high}$ to transform to the wire form 50a to a first austenitic shape. The first austenitic shape includes a first austenitic arcuate portion of a first austenitic radius of curvature that is smaller than the first martensitic radius of curvature of the first martensitic arcuate portion of the first martensitic shape. In other words, the transformation from martensite to austenite moves at least an arcuate portion of the wire form 50a from a martensitic shape of higher radius of curvature toward a lower radius of curvature that is nearer or at the size of a radius of curvature of an arcuate portion of the memorized austenitic shape. Also, the transformation from martensite to austenite moves the first tip portion 152 apart from the second tip portion 252. The heating to the higher second temperature above $A_{high}$ can occur from the introduction of electrical current from the power supply 84 into the wire form 50a to heat the wire form 50a due to the resistivity of the wire form 50a. The wire form 50a then cools down to body temperature which is above $M_{high}$ such that the wire form 50a remains in the austenitic shape. The shape transformation in this version of the invention is depicted in FIG. 12C. In the "as supplied" martensitic shape of FIG. 12C, the radius of curvature for the wire form 50a is greater than the radius of curvature for the "after heating" austenitic shape of the wire form 50a. In addition, in the "as supplied" martensitic shape of FIG. 12C, the first tip portion 152 is adjacent the second tip portion 252 at the separation line 153 whereas the first tip portion 152 is spaced apart from the second tip portion 252 for the "after heating" austenitic shape of the wire form 50a. In FIG. 12C, the first tip portion 152 and the second tip portion 252 form a somewhat Y-shape for the "after heating" austenitic shape of the wire form 50a. The wire form 50a opens at the tip 52a to lock itself into bone.

Thus, the invention provides methods and devices for the fixation of small bone fractures such as fractures of the phalangeal, metacarpal, and metatarsal bones.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

INDUSTRIAL APPLICABILITY

The invention provides methods and devices for the fixation of fractures of the phalangeal, metacarpal, and metatarsal bones.

What is claimed is:
1. A method for fixing a bone having a fracture, the method comprising:
  providing a wire comprising a shape memory alloy that has an austenitic phase structure above a first temperature and a martensitic phase structure below a second tem- perature, the wire being provided in the martensitic phase structure in a shape including an arcuate portion having a first radius of curvature; and inserting the wire into an intramedullary canal of the bone such that a first end of the wire is positioned on a distal side of the fracture and a second end of the wire is positioned on a proximal side of the fracture, wherein during insertion or after insertion of the wire into the intramedullary canal of the bone, the wire is heated above the first temperature to convert the wire to the austenitic phase structure and transform the arcuate portion of the wire to a second radius of curvature less than the first radius of curvature, and wherein the wire has a chord length from a distal end to a proximal end of the wire, wherein the chord length has a first length when the wire is in the martensitic phase, wherein the chord length has a second length when the wire is in the austenitic phase, and wherein the second length is shorter than the first length, and wherein the first end of the wire terminates in a tip, and wherein the wire is non-segmented from the tip to the second end of the wire.

2. The method of claim 1 further comprising:

creating a guide bore in the bone to create a pathway from an outer surface of the bone to the intramedullary canal of the bone, wherein the guide bore is created by placing a drill guide having a drill bit guide hole over an end of the bone and advancing a drill bit through the drill bit guide hole and into the bone.

3. The method of claim 2 wherein:

the drill guide includes a wire hole and the drill guide is secured to the end of the bone by advancing a wire through the wire hole and into the bone.

4. The method of claim 1 wherein:

the wire is cut adjacent an outer surface of the bone after insertion of the wire into the intramedullary canal of the bone.

5. The method of claim 4 wherein:

a cut end of the wire is pushed to or below the outer surface of the bone after cutting the wire.

6. The method of claim 1 wherein:

the shape-memory alloy is a nickel-titanium shape-memory alloy.

7. The method of claim 1 wherein:

the wire is heated by applying electric current to the wire after insertion of the wire into the intramedullary canal of the bone.

8. The method of claim 1 wherein:

the bone is selected from phalangeal, metacarpal, and metatarsal bones.

9. A method for fixing a bone having a fracture, the method comprising:

providing a wire comprising a shape memory alloy that has an austenitic phase structure above a first temperature and a martensitic phase structure below a second temperature, the wire being provided in the austenitic phase structure in a shape including an arcuate portion;

cooling the wire below the second temperature such that the wire is in the martensitic phase structure; and deforming the arcuate portion of the wire to a first radius of curvature before or during inserting the wire into an intramedullary canal of the bone such that a first end of the wire is positioned on a distal side of the fracture and a second end of the wire is positioned on a proximal side of the fracture, wherein during insertion or after insertion of the wire into the intramedullary canal of the bone, the wire is heated above the first temperature to convert the wire to the austenitic phase structure and transform the arcuate portion of the wire to a second radius of curvature less than the first radius of curvature, and wherein the wire has a chord length from a distal end to a proximal end of the wire, wherein the chord length has a first length when the wire is in the martensitic phase, wherein the chord length has a second length when the wire is in the austenitic phase, and wherein the second length is shorter than the first length, and wherein the first end of the wire terminates in a tip, and wherein the wire is a non-segmented from the tip to the second end of the wire.

10. The method of claim 9 further comprising:

creating a guide bore in the bone to create a pathway from an outer surface of the bone to the intramedullary canal of the bone, wherein the guide bore is created by placing a drill guide having a drill bit guide hole over an end of the bone and advancing a drill bit through the drill bit guide hole and into the bone.

11. The method of claim 10 wherein:

the drill guide includes a wire hole and the drill guide is secured to the end of the bone by advancing a wire through the wire hole and into the bone.

12. The method of claim 9 wherein:

the wire is cut adjacent an outer surface of the bone after insertion of the wire into the intramedullary canal of the bone.

13. The method of claim 12 wherein:

a cut end of the wire is pushed to or below the outer surface of the bone after cutting the wire.

14. The method of claim 9 wherein:

the shape-memory alloy is a nickel-titanium shape-memory alloy.

15. The method of claim 9 wherein:

the wire is heated above the first temperature by body heat after insertion of the wire into the intramedullary canal of the bone.

16. The method of claim 9 wherein:

the bone is selected from phalangeal, metacarpal, and metatarsal bones.

* * * * *